(12) United States Patent
Harvey

(10) Patent No.: US 9,554,986 B2
(45) Date of Patent: Jan. 31, 2017

(54) ORAL CARE COMPOSITION

(71) Applicant: Nelson Harvey, Amarillo, TX (US)

(72) Inventor: Nelson Harvey, Amarillo, TX (US)

( * ) Notice: Subject to any disclaimer, the term of this patent is extended or adjusted under 35 U.S.C. 154(b) by 0 days.

(21) Appl. No.: 14/447,385

(22) Filed: Jul. 30, 2014

(65) Prior Publication Data

US 2016/0030331 A1  Feb. 4, 2016

(51) Int. Cl.
| | |
|---|---|
| *A61K 8/99* | (2006.01) |
| *A61K 8/97* | (2006.01) |
| *A61K 8/26* | (2006.01) |
| *A61K 8/19* | (2006.01) |
| *A61K 8/22* | (2006.01) |
| *A61K 8/365* | (2006.01) |
| *A61K 8/66* | (2006.01) |
| *A61Q 11/00* | (2006.01) |
| *A61K 8/92* | (2006.01) |

(52) U.S. Cl.
CPC . *A61K 8/99* (2013.01); *A61K 8/19* (2013.01); *A61K 8/22* (2013.01); *A61K 8/26* (2013.01); *A61K 8/365* (2013.01); *A61K 8/66* (2013.01); *A61K 8/922* (2013.01); *A61K 8/975* (2013.01); *A61Q 11/00* (2013.01)

(58) Field of Classification Search
CPC .................................................. A61K 35/74
USPC .................................. 424/93.3, 440, 50, 49
See application file for complete search history.

(56) References Cited

U.S. PATENT DOCUMENTS

| | | | | |
|---|---|---|---|---|
| 6,080,401 A | * | 6/2000 | Reddy | A61K 36/235 424/725 |
| 2009/0274660 A1 | * | 11/2009 | Girsh | 424/93.3 |
| 2011/0104239 A1 | * | 5/2011 | Knutsen et al. | 424/440 |
| 2013/0344010 A1 | * | 12/2013 | Pompejus | A23L 1/3014 424/50 |
| 2015/0030546 A1 | * | 1/2015 | O'Malley | 424/49 |

* cited by examiner

*Primary Examiner* — Walter Webb
(74) *Attorney, Agent, or Firm* — Wilson Daniel Swayze, Jr.

(57) ABSTRACT

The present invention relates an oral care composition, comprising one or more functional agents selected from a group consisting of a whitening agent, a re-mineralizing agent, an anti-plaque agent, an anti-gingivitis agent, a detoxifying agent and its combinations. The composition further comprises a probiotic blend consisting of beneficial oral bacterial population and at least one essential oil comprising antimicrobial activity.

5 Claims, No Drawings

ORAL CARE COMPOSITION

FIELD OF THE INVENTION

The present invention relates to a composition for oral care and dental hygiene, in particular, to a multi-benefit, natural oral care composition that whitens teeth, re-mineralizes enamel and acts against gingivitis and plaque thereby prevents from the resulting periodontal disease.

BACKGROUND OF THE INVENTION

Oral hygiene is one of the most important aspects of personal care among consumers. Consumers all over the world use different types of products for oral care as a part of maintaining dental hygiene. People routinely brush their teeth with a toothbrush and a dentifrice which includes toothpaste or toothpowder or mouthwash at least two times a day. Use of such brushing ensures maintaining good oral hygiene by minimizing oral bacteria that accumulate in the mouth over the course of sleeping in the night or during the course of the day when people eat their food and consume beverages. Brushing regularly thus minimizes problems like cavities, tartar, gingivitis, caries, and bad breath, also known as halitosis.

In spite of brushing teeth twice a day, many people suffer from various forms of one or more of the above named diseases associated with dental hygiene and this is believed to be caused by bacteria acting in the oral mucosa over about twelve hour period between brushing period. In addition, Problems relating to teeth are also caused by cavity formation, dental caries, and chemical dissolution caused by acids, or erosion. These continue to be a major dental health problem among adults. Due to various factors, caries in particular is increasingly a problem for the ageing adult population who still have their own teeth. Such factors include impaired motor coordination, lack of motivation, reduced salivary secretion and use of medication or general ill health.

Dental plaque occurs in the form of a film, on virtually all dental surfaces. It is a by-product of microbial growth, and comprises a dense microbial layer consisting of a mass of microorganisms embedded in a polysaccharide matrix. Plaque itself adheres firmly to dental surfaces and is removed only with difficulty even through a rigorous brushing regimen. Moreover, plaque rapidly reforms on the tooth surface after it is removed. Plaque may form on any part of the tooth surface, and is found particularly at the gingival margin, in cracks in the enamel, and on the surface of dental calculus. The danger associated with the formation of plaque on the teeth lies in the tendency of plaque to build up and eventually produce gingivitis, periodontitis and other types of periodontal disease, as well as dental caries and dental calculus.

Gingivitis is characterized by inflammation or infection of the gums and the alveolar bones that support the teeth. Gingivitis is generally believed to be caused by bacteria in the mouth (particularly the bacteria instigated in plaque formation) and the toxins formed as by-products from the bacteria. The plaque and bacterial toxins are believed to be the causative agents for oral tissue inflammation within the mouth. Periodontitis is a progressively worsened state of disease as compared to gingivitis, where the gums are inflamed and begin to recede from the teeth and pockets begins to form in the recession, which ultimately may result in destruction of the bone and periodontal ligament. Thus, chronic infection and inflammation potentially results in subsequent loss of teeth.

Human periodontal diseases are inflammatory disorders that are result of complex interactions between oral pathogens and the host's immune response. It is believed that there are two interrelated aspects to the progression of periodontal disease, the first is the activation of the immune system of the host and the second is the production of oxygen radicals and their related metabolites. Increased production of oxygen radicals may contribute to oxidative stress, which is believed to be involved in periodontal disease. It is well established that tooth decay, development of plaque, plaque build-up, gingivitis, periodontal disease and other conditions of the oral cavity are associated with pathogens such as *Actinobacillus actinomycetemcomitans*, *Porphyromonas gingivalis*, *Actinomyces naeslundii*, and/or *Streptococcus mutans*, among many others.

Oral cleansing can prevent not only dental caries but also periodontosis. Conventional oral cleaning is done by brushing the teeth and using dentifrice products such as tooth paste, toothpowders and mouthwash, in order to improve the cleaning effect on teeth, remove dental plaque and prevent dental caries.

In solving the above oral care problems, the approach so far has been to use synthetic materials (e.g. Triclosan) in oral care products, which are believed by many consumers to be harsh on them. Consumers in recent times are gathering more awareness towards the harmful effects of synthetic ingredients used in dental hygiene products and prefer using products that contain natural materials. Further, in many countries, culturally or otherwise, people are reluctant to using alcohol in their mouthwashes. In addition, oral care products containing fluoride can also lead to serious health concerns other than dental fluorosis.

Oral care compositions containing a variety of active ingredient combinations are disclosed in a number of prior art publications. U.S. Patent publication US20130295027 discloses an oral care composition comprising antimicrobial essential oil. PCT publication WO2002092028 A2 shows an oral care composition comprising oral care actives and antibacterial plant extract. U.S. Pat. No. 8,715,625 discloses natural oral care composition with a limited number of naturally derived, naturally processed safe ingredients. U.S. Pat. No. 6,645,472 relates to a tooth and gum powdered dentifrice formulated with multiple ingredients acting synergistically. U.S. Patent publication US20060198795 A1 discloses a multi-component oral care composition for enhancing the effects of tooth whitening and or cleaning.

Conventional oral care products generally employ synthetic agents as active ingredients such as triclosan, sodium lauryl sulphate and toxic agents such as sodium fluoride, artificial dyes and hydrated silica in addition to other chemical substances. Furthermore, procuring and usage of separate oral care products for cleansing, whitening, re-mineralization, anti-plaque, anti-gingivitis activity and antibacterial activity proves to be cumbersome and expensive. Further limitations of the prior art oral care compositions includes inefficient removal of toxins, inefficient action against tooth decay and gum infections.

In spite of all these approaches and attempts to provide oral care compositions for dental hygiene, it remains desirable to provide still an improved oral care composition made from naturally occurring products for complete dental care including tooth whitening, enamel repair, activity against gingivitis and plaque.

SUMMARY OF THE INVENTION

The present invention discloses an oral care composition, comprising one or more functional agents selected from a group consisting of a whitening agent, a re-mineralizing agent, an anti-plaque agent, an anti-gingivitis agent, a detoxifying agent and any of its combinations; a probiotic blend comprising beneficial oral bacteria; and at least one essential oil comprising antimicrobial activity.

In another embodiment, the present invention discloses a method for cleansing, re-mineralizing, reducing plaque, disinfecting and treating surrounding gums and tissues comprising: i) providing an oral care composition comprising one or more functional agents selected from a group consisting of a whitening agent, a re-mineralizing agent, an anti-plaque agent, an anti-gingivitis agent, a detoxifying agent, a probiotic blend, antimicrobial essential oil and any of its combinations; ii) placing an effective amount of the oral care composition in oral cavity or in contact with a toothbrush; iii) brushing the teeth and surrounding gums and tissues in the oral cavity using the oral care composition; iv) swishing the oral care composition around in the oral cavity and thereafter expectorating the composition.

Still other embodiments of the present invention will become readily apparent to those skilled in the art from the following detailed description, wherein are described embodiments by way of illustrating the best mode contemplated for carrying out the invention. As will be realized, the invention is capable of other and different embodiments and its several details are capable of modifications in various obvious respects, all without departing from the spirit and the scope of the present invention. Accordingly, the detailed description is to be regarded as illustrative in nature and not as restrictive.

DETAILED DESCRIPTION OF THE INVENTION

The oral care composition of the present invention can comprise, consist of, or consist essentially of the essential elements and limitations of the invention described herein, as well any of the additional or optional ingredients, components, or limitations described herein.

According to the present invention, the oral care composition comprises one or more functional agents selected from a group consisting of a whitening agent, a re-mineralizing agent, an anti-plaque agent, an anti-gingivitis agent, a detoxifying agent and any of its combinations. In addition, the composition further comprises a probiotic blend comprising beneficial oral bacteria and at least an essential oil with antimicrobial activity.

The whitening agent comprises of abrasives, cleansing agents and dental bleach. As a person ages the adult teeth often become darker due to changes in the mineral structure of the tooth, decrease in enamel porosity and phosphate-deficiency. Teeth can become stained by bacterial pigments, foods and vegetables rich in carotenoids or xanthonoids. Certain antibacterial medications (eg: tetracycline) can also cause teeth stains or a reduction in the lustre of the enamel. Ingesting colored beverages like coffee, tea, red wine and usage of tobacco can discolor teeth and oral cavity to a great extent. The whitening agent in the present oral care composition comprises sodium bicarbonate, calcium peroxide, sodium phosphate and Himalayan pink salt. The resulting degree of whiteness can be compared and studied using standard shades of whiteness for teeth.

In an embodiment of the present invention, the oral care composition further comprises a nutritional supplement consisting Norwegian kelp (*Ascophyllum nodosum*). Norwegian kelp posses a wide array of nutrients including polysaccharides, amino acids, proteins, organic acids and minerals such as potassium, phosphorous, calcium, magnesium, sodium, manganese, zinc, iron, copper, iodine, and nitrogen. It further comprises essential vitamins such as vitamin K, A, D, E, B1, B2, B12, folate and niacin.

Norwegian kelp is used in the form of powder, also acts as a natural detoxifying agent that flushes out heavy metals like barium, cadmium and plutonium from our body. It is also rich in sodium alginate which helps in protecting the body from radioactive metals. All of the nutrients in Norwegian kelp show high bioavailability due to its phytomatrix form. The body recognizes these nutrients and immediately absorbs and utilizes them, unlike synthetic supplements which are not as readily absorbed and end up being eliminated.

The re-mineralizing agent in the present oral care composition re-mineralizes cavities, cracks and tooth enamel. It comprises sodium bicarbonate, Norwegian kelp, bentontite clay, calcium lactate and zinc citrate. Tooth enamel is a thin, hard material that covers the dentin, or main body of teeth, and protects it from harsh temperatures. Tooth enamel that has suffered minor damage from acid erosion or mechanical wear and tear can be self restored by a process called mineralization. But, problems arising from poor dietary habits and/or oral hygiene habits outpace the natural re-mineralizing process resulting in a need for re-mineralizing treatment as a part of oral hygiene routine.

Anti-plaque agent and anti-gingivitis agent of the present oral care composition comprise enzymes derived from plant material such as papain and bromelain. These enzymes are basically proteinases which would help in digesting the protein stuck in between the teeth. It also digests plaque and helps in reducing inflammation of gums, thereby acting against gingivitis. The anti-gingivitis agent repairs gum tissue and stimulates surrounding tissue growth, tightens loose teeth and thereby prevents from resulting periodontal disease.

The detoxifying agent comprises bentontite clay. Bentontite Clay possesses a very strong negative ionic charge which attracts things that have a positive charge, such as heavy metals, toxins, harmful bacteria, pesticides, and other pathogens. Bentontite clay is also used to control dry mouth and tooth sensitivity. The oral care composition comprises of pure, natural and non-toxic ingredients in the formulation in contrast to the conventional oral care products containing toxic agents such as fluoride, triclosan, Sodium lauryl sulphate, silica and the like.

Oral probiotics play an integral part in the fight against tooth decay, gum disease and bad breath. The use of oral probiotics is a healthy method for reducing infective oral bacterial population along with reduction in tooth decay and gum disease. It also helps in protecting from acquiring new infections caused by other harmful microorganisms. Probiotic blend in the present oral care composition comprises a mixture of beneficial oral bacterial population selected from *L. rueteri, L. fermentum, L. rhamnosus, S. thermophilus, S. salivarius* and its combinations thereof.

In an embodiment, the essential oil or antimicrobial essential oil in the present oral care composition is selected from a group consisting of clove oil, cinnamon oil, peppermint oil, sesame oil, oregano oil and any of its combinations. The essential oil shows antimicrobial activity against harmful pathogens such as *Streptococcus mutans* growth.

In another embodiment, the oral care composition comprises an effective amount of calcium lactate, which prevents tooth decay and strengthens teeth. Zinc citrate, which acts as against plaque formation and thereby prevents from periodontal disease. Xylitol, a sweetening agent, which also acts as antimicrobial agent.

In addition to the above discussed ingredients, the oral care composition may also contain optional ingredients. The optional ingredients may comprise flavouring substances, sweetener, coloring agent, astringent, antioxidant, binder, thickener, bulking agent, desensitizing agent, preservative and any other ingredient known to those skilled in the art.

The oral care composition of the present invention can be prepared in different forms of dentifrice such as toothpaste, toothpowder, mouthwash, oral spray, denture cleanser, dental gel, chewing gum and any other form generally known to those skilled in the art.

The oral care composition of the present invention, in addition to the above oral care benefits such as whitening, enamel repair, plaque control, stimulating gum tissue, also acts against oral malodour and results in fresh breath.

In another embodiment, the present invention relates to a method for cleansing, re-mineralizing, reducing plaque, disinfecting and treating surrounding gums and tissues, the method comprising: i) providing an oral care composition; ii) placing an effective amount of the oral care composition in oral cavity or in contact with a toothbrush; iii) brushing the teeth and surrounding gums and tissues in the oral cavity using the oral care composition; iv) swishing the oral care composition around in the oral cavity for a period of time before expectorating the composition.

According to an embodiment, a method for cleansing, re-mineralizing, reducing plaque, disinfecting and treating surrounding gums and tissues comprises i) placing a quarter size of the oral care composition in oral cavity or in contact with a toothbrush; ii) brushing softly the teeth and surrounding gums and tissues in the oral cavity for 2 minutes iii) clear mouth and rinse after 2 more minutes.

The oral care composition of the present invention can be used for oral hygiene routine using methods known in the art for teeth whitening, enamel repair or re-mineralization, teeth cleansing, detoxifying and protecting from plaque and gingivitis.

EXAMPLE

Example 1

The oral care composition of the present invention comprises the following ingredients according to an exemplary embodiment.

Ingredients: Sodium bicarbonate, xylitol, calcium peroxide, bentonite clay, sesame oil, papain, calcium lactate, probiotic blend (*L. rueteri, L. fermentum, L. rhamnosus, S. thermophilus* and *S. salivarius*), sodium phosphate, zinc citrate, bromelain, peppermint oil, cinnamon oil, clove oil, oregano oil, kelp powder (Norwegian kelp) and Himalayan pink salt.

What is claimed is:

1. An oral care composition, comprising:
   One or more functional agents selected from a group consisting of an anti-plaque agent, an anti-gingivitis agent and any of its combinations;
   a probiotic blend comprising beneficial oral bacteria; and
   at least one essential oil comprising antimicrobial activity;
   a nutritional supplement comprising Norwegian kelp;
   wherein the oral care composition is only a powder.

2. The composition of claim 1, wherein the probiotic blend comprises of bacteria selected from a group consisting of *L. rueteri, L. fermentum, L. rhamnosus, S. thermophilus, S. salivarius* and its combinations thereof.

3. The composition of claim 1, wherein the essential oil is selected from a group consisting of clove oil, cinnamon oil, oregano oil, peppermint oil, sesame oil and its combinations thereof.

4. The composition of claim 1, wherein the anti-plaque agent and the anti-gingivitis agent comprises enzymes to digest plaque and act against gingivitis.

5. The composition of claim 4, wherein the enzymes are selected from a group consisting of bromelain, papain and its combinations thereof.

* * * * *